United States Patent
Ryu et al.

(10) Patent No.: US 9,308,059 B2
(45) Date of Patent: Apr. 12, 2016

(54) IMPLANT BITE REGISTRATION JIG AND BITE IMPRESSION FABRICATION METHOD USING THE JIG

(75) Inventors: Jae Ho Ryu, Busan (KR); Tae Hyun Gong, Busan (KR); Moo Yong Park, Busan (KR); Kwang Hoon Lee, Gyeonggi-do (KR)

(73) Assignees: Osstem Implant Co., Ltd., Seoul (KR); Kwang Hoon Lee, Gyeonggi-do (KR)

( * ) Notice: Subject to any disclaimer, the term of this patent is extended or adjusted under 35 U.S.C. 154(b) by 559 days.

(21) Appl. No.: 13/024,223

(22) Filed: Feb. 9, 2011

(65) Prior Publication Data
US 2012/0202169 A1    Aug. 9, 2012

(51) Int. Cl.
*A61C 8/00* (2006.01)
(52) U.S. Cl.
CPC .................... *A61C 8/0001* (2013.01)
(58) Field of Classification Search
CPC ........... A61C 8/0001; A61C 8/00; A61C 9/00
USPC .............................. 433/172–176, 75, 76, 214
See application file for complete search history.

(56) References Cited

U.S. PATENT DOCUMENTS

| | | | | |
|---|---|---|---|---|
| 5,052,929 A * | 10/1991 | Seal | | 433/173 |
| 5,213,502 A * | 5/1993 | Daftary | | 433/172 |
| 5,215,460 A * | 6/1993 | Perry | | 433/75 |
| 5,947,736 A | 9/1999 | Behrend | | |
| 2005/0266383 A1 * | 12/2005 | Aravena et al. | | 433/173 |
| 2008/0227057 A1 * | 9/2008 | Anitua Aldecoa | | 433/174 |
| 2011/0008755 A1 * | 1/2011 | Misch | | 433/176 |

FOREIGN PATENT DOCUMENTS

KR    20-0282986 Y1    7/2002

* cited by examiner

*Primary Examiner* — Cris L Rodriguez
*Assistant Examiner* — Mirayda A Aponte
(74) *Attorney, Agent, or Firm* — Seed IP Law Group PLLC

(57) ABSTRACT

An implant bite registration jig includes a coupling portion configured to produce a clear impression in bite impression material; a connecting portion that connects the implant jig with a fixture embedded in a patient's gums; and a body that is formed between the coupling portion and the connecting portion. The implant bite registration jig is positioned in an embedded fixture and a bite impression is taken. Reference marks are formed in the bite impression material by the registration jig, which permit accurate location of the fixture. This makes it possible to simultaneously take a dental impression and a bite impression in an implant operation, similar to a natural teeth operation, such that it is possible to reduce the cost and time for manufacturing a prosthesis.

6 Claims, 6 Drawing Sheets

(a)

(b)

(c)

(a)

(b)

(c)

IMPLANT BITE REGISTRATION JIG AND BITE IMPRESSION FABRICATION METHOD USING THE JIG

BACKGROUND

1. Technical Field

The present invention relates to an implant that is used to replace missing teeth of patients, particularly an implant bite registration jig in an implant procedure and a bite impression fabrication method using the jig.

2. Description of the Related Art

An implant is a prosthesis replacing a missing body part, but generally, in dentistry, refers to a prosthesis that restores the original function of missing teeth by embedding and fixing a fixture in the jawbone with natural teeth missing such that a denture is fixed, in order to replace the root of the missing teeth.

The implant is classified in various types, depending on the coupling type of the denture and the tooth root, in which a typical coupling is a screw type implant using a screw. A screw type implant of the related art is shown in FIG. 1.

The screw type implant system of the related art shown in FIG. 1 is called an octa abutment system, for the octagonal head of an abutment. The abutment system of the related art shown in FIG. 1 is composed of a fixture 110, an abutment 120, a cylinder 130, a screw 140, and prosthesis 150.

The fixture 110 is embedded in the jawbone and fixes the implant system and it is made of titanium having good biocompatibility for amalgamating with the bone tissue of a human body. The fixture 110 has an abutment-fastening hole 111, an abutment seat hole 112, and a fixture body 113.

The abutment-fastening hole 111 is formed to be axial in the fixture 110 such that the abutment 120 can be fastened to the fixture 110. A thread is formed in the inner circumference of the abutment-fastening hole 111, such that the abutment 120 is screw-fastened. The abutment seat hole 112 is axially formed to be narrower downward in the fixture 110 and ends with a step 112a. The abutment seat hole 112 is connected to the abutment-fastening hole 111 through the step 112a. The fixture body 113 has a thread on the outer circumference.

The abutment 120 is combined with the fixture 110, supporting and fixing the cylinder 130, and has a head 121, a body 122, a threaded-portion 123, and a screw-fastening hole 124.

The head 121 is a polygon and formed on the top of the body 122. The body 122 is formed to be narrower downward under the head 121 and has a step 122a at the top, such that the body 122 is separated from the head 121.

The threaded-portion 123 is formed under the body 122 and screw-fastened in the abutment-fastening hole 111 of the fixture 110.

Further, the screw-fastening hole 124 is formed through the head 121 and the body 122 and has a thread on the inner circumference such that a screw 140 is screw-fastened.

The cylinder 130 is seated on the head 121 and the step 122a of the abutment 120 and supports the prosthesis 150, and has an outer circumference 131, a screw seat hole 132, and an abutment seat hole 133.

The outer circumference 131 has a shape narrowing upward, and a cut-off surface 131a is formed at the upper portion of the outer circumference 131 and an edge 131b is formed at the lower end. The screw seat hole 132 is formed in the cylinder 130. The abutment seat hole 133 where the head 121 of the abutment 120 is seated is coaxially formed under the screw seat hole 132. The abutment seat hole 133 has shape corresponding to the head 121 (a polygon, e.g., a hexagon or a octagon).

The screw 140 is screw-fastened in the screw-fastening hole 124 of the abutment 120 to fasten the cylinder 130 to the abutment 120 and is composed of a head 141 and a body 142.

The head 141 has a cylindrical shape and a driver coupling hole 141a is formed at the upper portion. The body 142 extends from the bottom of the head 141 and has a thread 142a having a predetermined length at the lower portion.

The prosthesis 150 is manufactured by taking an impression, manufacturing a model, manufacturing, embedding, and burning a mold, and forming a screw access hole 153. The screw access hole 153 is formed in a cylindrical shape passing through the central portion of the prosthesis 150, and into which a screw 140 is inserted when the prosthesis is placed in the mouth.

The process of making and installing an implant having the configuration described above includes, first, embedding the fixture in the patient's gums. A healing period is generally employed to permit the bone to firmly anchor the fixture. During this time, a prosthesis is made, which is to be coupled to the fixture. To make the prosthesis, a dental impression is taken at the time the fixture is embedded, and a model of the patient's teeth is made from the dental impression. Based on the model, the implant is made, including manufacturing a mold and casting an inner pipe, forming the contour by porcelain restoration, and bonding the prosthesis for attaching the prosthesis to the contour with cement.

A bite impression is taken, which provides information on relative positions of the upper and lower teeth when they close. This is necessary in manufacturing the prosthesis, to ensure that the prosthesis correctly fits with the other teeth, especially when the patient bites. Taking the bite impression is generally performed after the dental impression is taken that patterns the conditions of the inside of the patient's mouth. The bite impression is sent with the dental impression to a dental laboratory so as to manufacture a prosthesis.

In the case where a portion of a tooth remains in the position of a natural tooth, the portion can be used as a support for a prosthesis or crown, such that when a bite impression is taken, it will show the location and shape of the tooth portion, so that a dental lab can make the prosthesis that will correctly fit.

Taking the bite impression is a necessary part of providing an implant, also in the case where a tooth is extracted and a fixture that is a tooth root is embedded. In this case, since the tooth has been extracted and the fixture has been embedded substantially in parallel with the surface of the gums, there is no rigid structure from which the bite material can take an impression to show the position and alignment of the fixture.

Therefore, in the related art, as shown in FIG. 2, (a) a dental impression is taken at a hospital, (b) the impression is sent to a dental laboratory, (c) a model is manufactured, and (d) a specific support, that is, a jig for taking the impression of the bite is manufactured from the model.

As described above, the jig that has been manufactured in the dental laboratory is sent back to the hospital and the patient comes to the hospital, (e) the separately manufactured jig is mounted in the patient's mouth, (f) a bite impression is taken by injecting a bite material, (g) the bite is sent back to the dental laboratory, and (f) the prosthesis is manufactured by using the bite as a guide.

The prosthesis manufactured in the dental laboratory is sent to the hospital, the patient comes to the hospital, and the prosthesis is mounted in the patient's mouth, thereby completing the implant operation.

As described above, since it is required to specifically manufacture a jig for supporting in the dental laboratory, send it to the dental clinic, and take a bite impression from the patient who has come to the clinic, in order to take a bite impression in the operation of making an implant, it takes a long time to complete the operation and the patient has to live a long time, without a tooth.

Further, there is no exclusive material for a jig for supporting a bite impression, other expensive products, such as Mount, Temporary Abutment, UCLA Abutment, are used to manufacture the jig, such that the manufacturing cost and period are increased.

That is, it is required to manufacture a support, using a specific product out of the use and the patient should come to the dental clinic once again in order to take a bite impression, and the period of manufacturing the prosthesis is correspondingly increased.

BRIEF SUMMARY

One embodiment provides an implant bite registration jig and a bite impression fabrication method using the jig, which can reduce the cost and time for manufacturing the prosthesis by making it possible to simultaneously take a dental impression and a bite impression in an implant operation, similar to a natural tooth operation.

According to an embodiment, there is provided an implant bite registration jig including: a coupling portion that supports a bite material; a connecting portion that connects the implant jig with a fixture embedded in advance in the gums; and a body that is formed between the coupling portion and the connecting portion.

The top of the coupling portion may be flat or slightly convex upward, and smooth without prominences and depressions.

The outer circumference of the coupling portion may have a constant diameter to facilitate separating and positioning a hardened bite material, or have a shape of which the diameter gradually changes such that the diameter at the middle portion is larger than the diameter at the top.

The body may have a diameter the same or smaller than the diameter of the coupling portion in order to minimize interference from the gums or the adjacent teeth.

All the edges on the outer sides of the coupling portion and the body may be rounded.

The connecting portion may have a threaded portion with a thread to be fastened to a fixture embedded in advance in the gums.

The connecting portion and the fixture may be coupled by any appropriate structure, including, for example, thread-fastening, snap-fitting, and friction-fitting.

The implant jig may have a driver seat hole that is formed through the top of the coupling portion to insert a fastening tool when assembling or separating the implant jig with or from the fixture.

The fastening tool may also be used for implant operation and the driver seat hole may be sized such that the fastening tool is friction-fitted.

A bored portion having a diameter larger than the driver seat hole may be formed at the inlet of the driver seat hole.

The bored portion may be tapered or stepped.

The coupling portion and the body may be formed in an outer body member that is one unit having a through-hole and the connecting portion is implemented by a connecting member that is another one unit coupled to a fixture through the through-hole.

The though-hole formed in the outer body member may have a small-diameter body portion having a first diameter, a large-diameter body portion formed at the coupling portion and having a second diameter, larger than the first diameter, and a tapered body portion that is formed between the large-diameter body portion and the small-diameter portion body to gradually decrease in diameter.

The connecting member may have a small-diameter connection portion having a diameter corresponding to the small-diameter body portion, a large-diameter connection portion having a diameter corresponding to the large-diameter body portion, a tapered connection portion having a shape corresponding to the tapered body portion, and a threaded-portion having a thread to be fastened to a fixture embedded in the gums.

Therefore, with the tapered connection portion of the connecting member in contact with the tapered body portion of the outer body member, the outer body can be fixed on the fixture by fastening the threaded portion of the connecting member to the fixture.

Further, according to another embodiment, there is provided an implant bite registration jig, wherein a top that supports a bite material by being detachably coupled to a fixture embedded in advance in the gum is positioned close to the opposite teeth.

Further, according to another embodiment, there is provided a bite impression fabrication method, wherein a prosthesis is manufactured by fastening the impression taken with a fixture embedded in the gum and the implant jig described above, and using a bite impression taken by injecting a bite material.

It is to be understood that both the foregoing general description and the following detailed description are exemplary and explanatory and are intended to provide further explanation of embodiments of the invention as claimed.

BRIEF DESCRIPTION OF THE SEVERAL VIEWS OF THE DRAWINGS

The accompanying drawings, which are included to provide a further understanding of the invention and are incorporated in and constitute a part of this specification, illustrate embodiments, and together with the description serve to explain the principles of the invention:

FIG. 5(*b*) is a front elevational view showing another example of an implant jig;

FIG. 5(*c*) is a front elevational view showing another example of an implant jig;

FIG. 7(*b*) is a front elevational view showing another example of an implant jig;

FIG. 7(*c*) is a front elevational view showing another example of an implant jig;

FIG. 8(b) is a view illustrating another step in the process of taking the bite impression;

FIG. 8(c) is a view illustrating another step in the process of taking the bite impression;

FIG. 8(d) is a view illustrating another step in the process of taking the bite impression;

FIG. 8(e) is a view illustrating another step in the process of taking the bite impression:

FIG. 8(f) is a view illustrating another step in the process of taking the bite impression; and FIG. 8(g) is a view illustrating another step in the process of taking the bite impression.

DETAILED DESCRIPTION

Hereinafter, an implant bite registration jig and a bite fabrication method using the jig according to various embodiments are described in detail with reference to the accompanying drawings.

Figure 1:
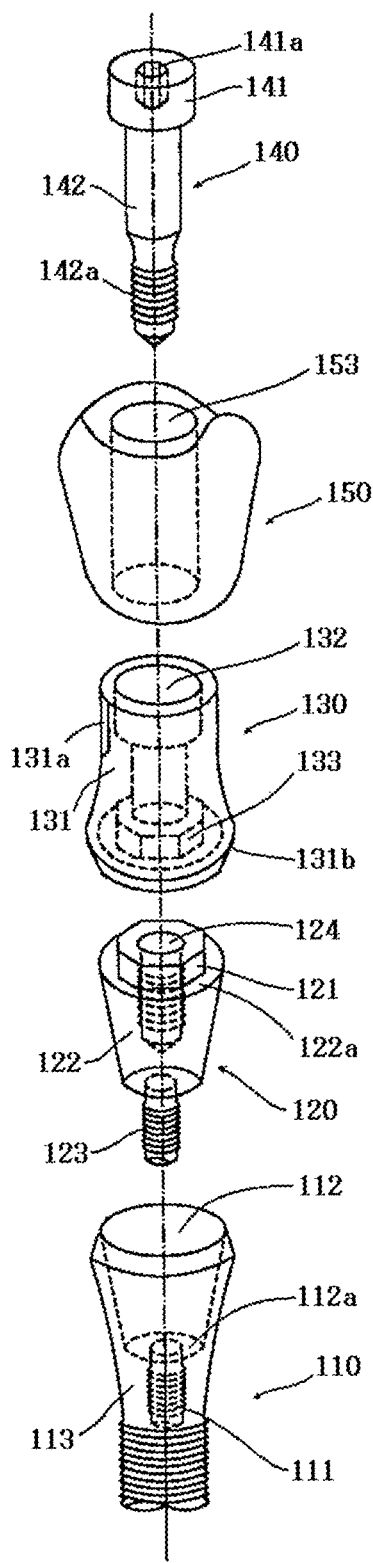
FIG. 1 is an exploded view showing the parts of an implant of the related art.
Figure 2:
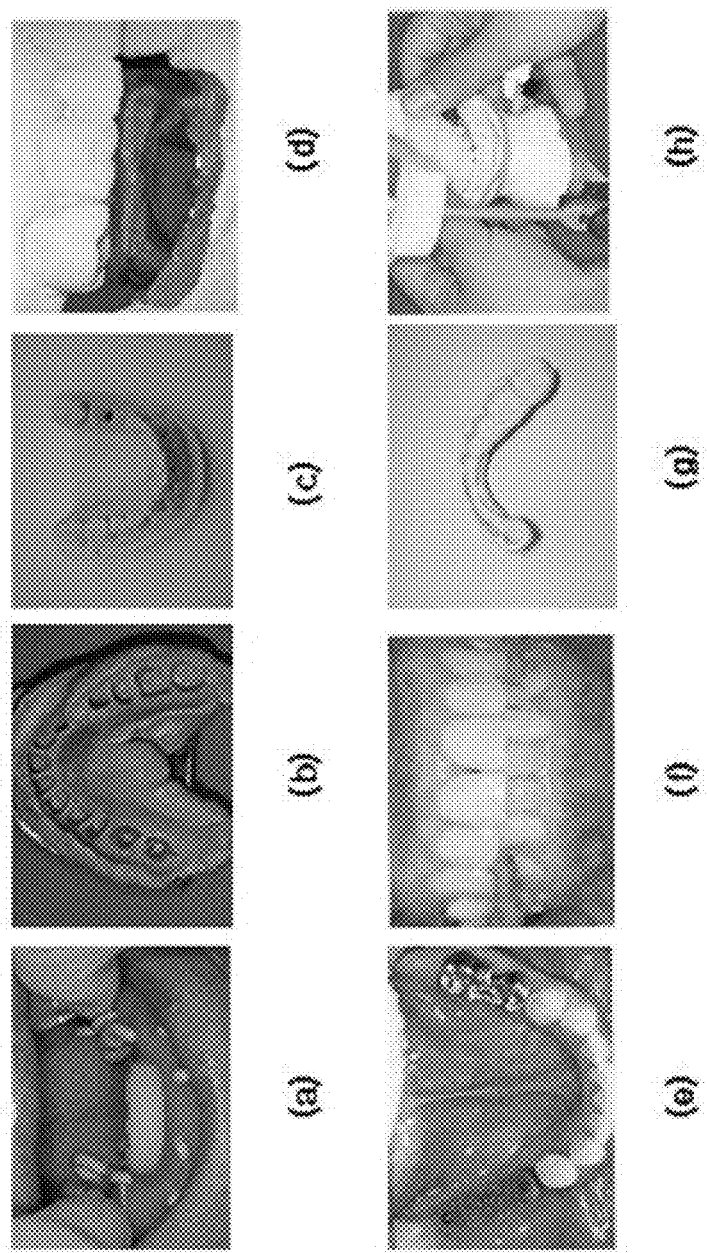
FIG. 2 is a view illustrating a process of taking a bite impression in a method of manufacturing the implant prosthesis of the related art.
Figure 3:
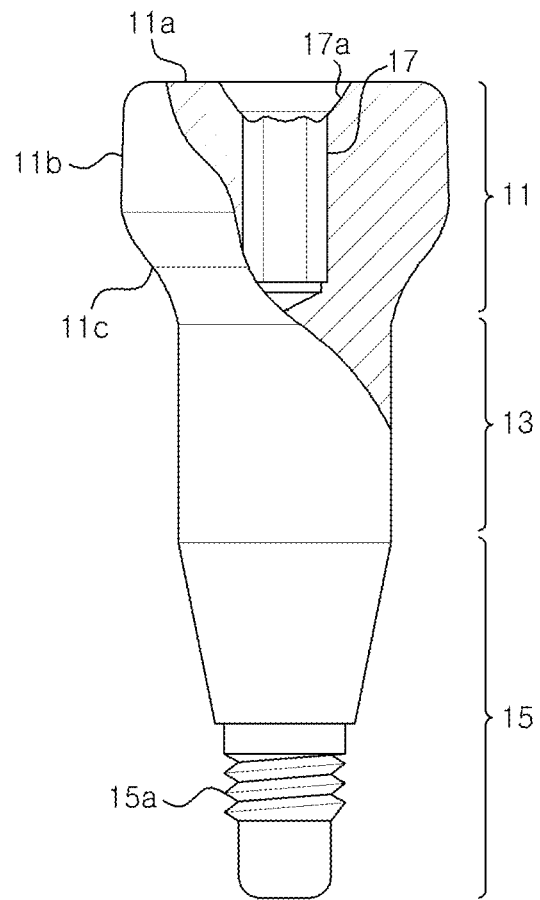
FIG. 3 is a partial cross-sectional view of an implant jig according to a first embodiment.

FIG. 3 shows an implant jig 10 according to a first embodiment. As shown in FIG. 3, the implant jig 10 includes a coupling portion 11 that support a bite material, a connecting portion 15 that is coupled to an embedded fixture, and a body 13 that is formed between the coupling portion 11 and the connecting portion 15.

The coupling portion 11 has a top 11a that can support the bite material. It is preferable that the top 11a is flat or slightly convex upward, and smooth without prominences and depressions.

It is preferable that the outer circumference 11b of the coupling portion 11 has a shape that decreases in diameter upward such that the diameter at the middle portion 11d is larger than the diameter at the top 11a in FIG. 3, because it is easy in this case to separate and accurately position the hardened bite material.

The body 13 is under the coupling portion 11 and has a diameter the same or smaller than the diameter of the coupling portion 11 to minimize interference from the gums or adjacent teeth. An inclined portion 11c that decreases in diameter downward is formed between the body 13 having a relatively smaller diameter and the outer circumference 11b of the coupling portion 11 having a relatively larger diameter, and smoothly connects the body 13 with the coupling portion 11.

It is preferable to round all the edges on the outer sides of the coupling portion 11 and the body 13, in order to prevent the gums or teeth in the mouth from being damaged.

Meanwhile, the thicker the bite material, the larger the error in manufacturing a prosthesis, such that it is preferable that the top 11a of the coupling portion 11 is positioned close to the opposite teeth. For this configuration, it is possible to the keep the bite material at a preferred thickness of 0.5~1.5 mm, by manufacturing the coupling portion 11 and the body 13, particularly the body 13 to have various lengths and using an implant jig having an appropriate length in accordance with the conditions of the patient's mouth.

The connecting portion 15 has a threaded portion 15a with a thread to be fastened to a fixture embedded in the gums. Obviously, the connecting portion 15 with the threaded portion 15a may be implemented in various shapes, corresponding to the shape of the fixture. The connecting portion 15 and the fixture may be coupled by structures other than thread-fastening, such as, e.g., snap-fitting and friction-fitting.

One or more drive seat hole 17 is formed through the top 11a of the coupling portion 11 such that a fastening tool, such as a driver, can be inserted to assemble or separate the implant jig with or from the fixture. The size and shape of the driver seat hole 17 may be determined such that the driver that is a fastening tool is engaged by friction. The drive seat hole 17 is formed to correspond to the sizes of the existing fastening tools that are used in the existing implant such that they can be used for both purposes.

Figure 4:
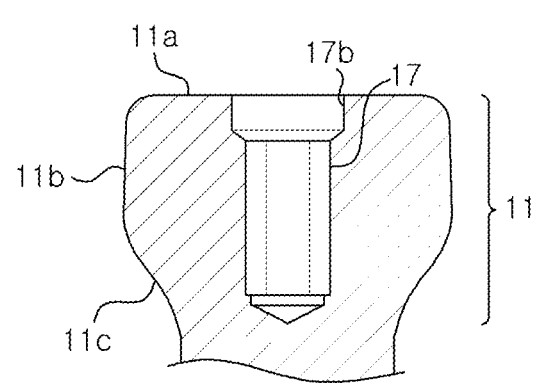
FIG. 4 is a view showing an example of the tapered portion formed around a driver seat hole of the implant jig according to another embodiment.

Bored portions 17a, 17b that are larger in diameter than the driver seat hole 17 are formed at the inlet of the driver seat hole 17. The bored portions 17a, 17b may be implemented in various shapes, as long as it has a larger diameter than the driver seat hole 17. For example, the bored portion 17a shown in FIG. 3 is tapered and the bored portion 17b shown in FIG. 4 is stepped.

According to an embodiment, since the bored portions 17a and 17b are formed at the inlet of the driver seat hole 17, when a bite material is provided on the coupling portion 11 of the implant jig for taking impression, the fluid bite material can flow into the driver seat hole 17 through the bored portions 17a and 17b, or only into the bored portions 17a and 17b, not in the driver seat hole 17.

If the bored portions 17a and 17b are not formed at the inlet of the driver seat hole 17, the fluid bite material directly flows into the driver seat hole 17 and the hardened bite has the shape of the driver seat hole, that is, a high hexagonal protrusion.

When only one implant assembly is mounted in the patient' mouth, possibility of errors due to the protrusion is small, but when a plurality of implant assemblies, for example, three or four implant assemblies are mounted, the hardened bites have a plurality of protrusions, such that possibility of errors due to the protrusions in the process of manufacturing prostheses increases. In other words, the bite material with a protrusion in taking impression may slightly deform while hardening. As shown in (g) of FIG. 8, it is required to manufacture the prosthesis by placing the bite in a model in consideration of the direction and position of a plurality of protrusions when manufacturing the prosthesis on the basis of the impression material and bite, such that possibility of errors in placing the bite in the model increases. Accordingly, the prosthesis that accurately fits the model may cause malocclusion in the patient's mouth.

Figure 8:
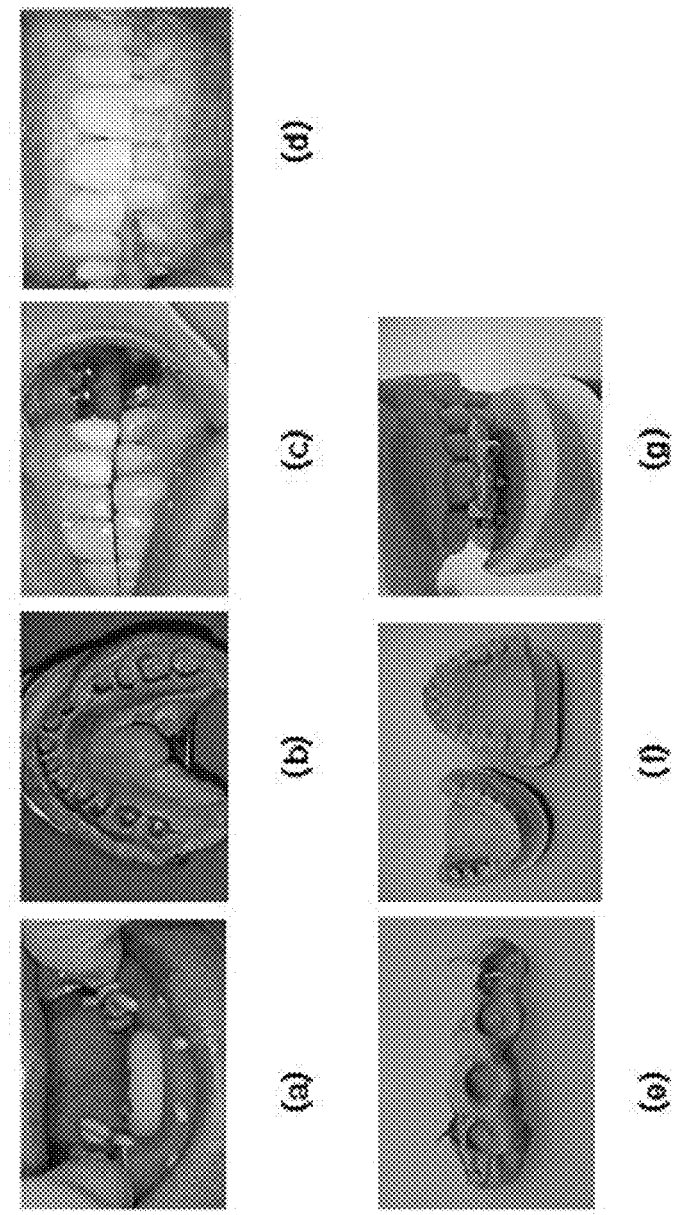
FIG. 8(*a*) is a view illustrating a step in a process of taking a bite impression for manufacturing an implant prosthesis according to one embodiment.

However, since the bored portions 17a and 17b are formed at the inlet of the driver seat hole 17, as shown in (e) of FIG. 8, a substantially circular low protrusion is formed, as compared with when the bored portions 17a and 17b are not formed. That is, assuming that the amount of material that flows into the driver seat hole 17 in taking a bite impression is the same when the bored portions 17a and 17b are formed and when they are not formed, the volume receiving the bite material can be increased by the volumes of the bored portions 17a and 17b, such that relatively small protrusions are formed.

When the protrusions are small, possibility of deformation in taking a bite impression or hardening the bite material decreases, and possibility of errors due to the protrusions in placing the bite in the model can be reduced even if a plurality of implant assemblies are mounted.

According to embodiments in which the bored portions 17a and 17b are formed at the inlet of the driver seat hole 17, it is possible to reduce errors when attaching/detaching the bite to/from the implant jig in the process of manufacturing the prosthesis after the bite material is hardened. That is, since the hardened protrusion of the bite impression is small, the bite impression can be accurately placed on the implant jig in the process of manufacturing the prosthesis, without interference.

FIGS. 5A-5C show various shapes of implant jigs according to the first embodiment. According to various embodiments, it is possible to manufacture and use various shapes of implant jigs, in accordance with the conditions of the patient's mouth or the types of fixtures. The implant jigs 10 shown in FIGS. 5A-5C illustrate variations in length, diameter, and shape to accommodate, for example, patients with longer or shorter teeth, and with more or less space in which to place the implant jig. Additionally, the implant jigs 10 are shown with various connecting portions 15 configured to couple with respective different types of fixtures previously implanted in a patient's gums. It will be recognized that the particular implant jigs shown are merely exemplary, to illustrate a few of the many modifications that can be provided to accommodate the specific requirements that can arise.

Hereinafter, an implant jig 20 according to a second embodiment is described with reference to FIGS. 6A-7C.

Figure 5:
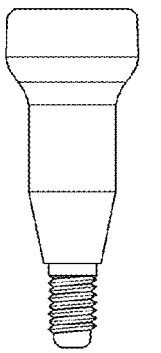
FIG. 5(*a*) is a front elevational view showing one example of an implant jig.
Figure 5:
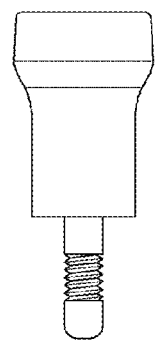
Figure 5:
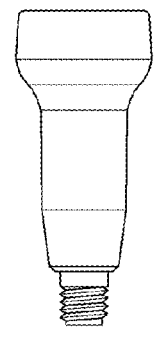
Figure 7:
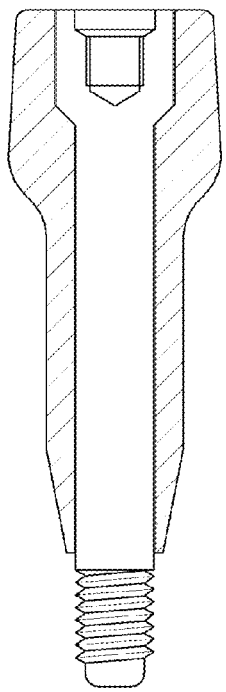
FIG. 7(*a*) is a front elevational view showing another example of an implant jig.
Figure 7:
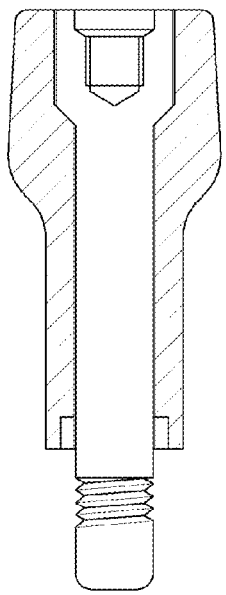
Figure 7:
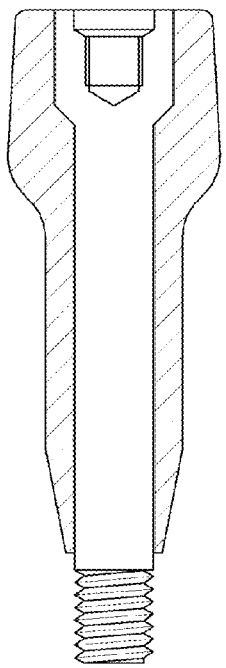
Figure 6:
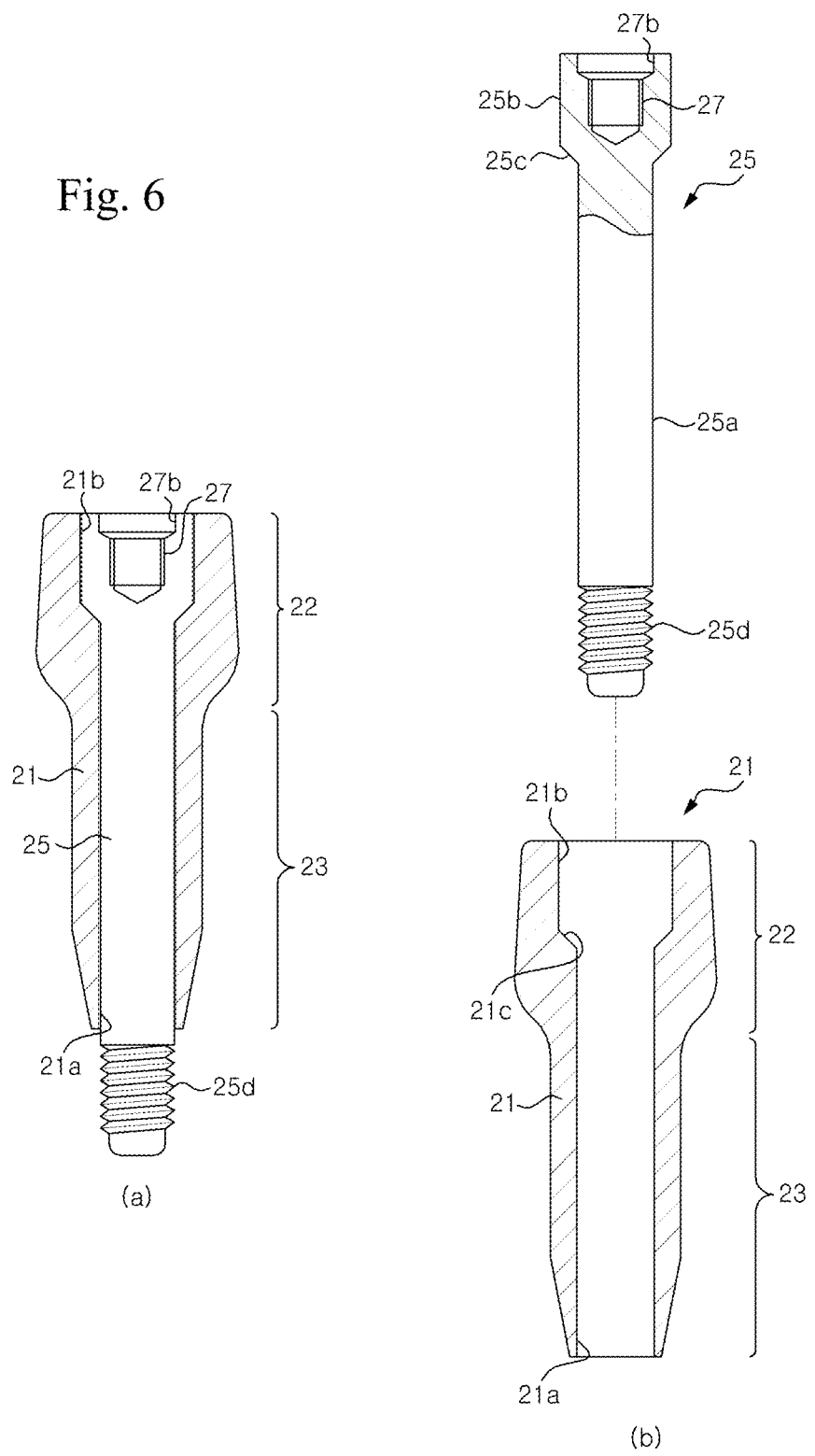
FIGS. 6A and 6B are partial cross-sectional views of an implant jig according to another embodiment.

Although only an integrated implant jig composed of the coupling portion 11, the body 13, and the connecting portion 15, which are formed in one unit is shown in FIGS. 3 to 5, if necessary, an implant jig may be manufactured in two parts, as shown in FIGS. 6A-7C. That is, the upper portions of the coupling portion 11, the body 13, and the connecting portion 15 of the first embodiment may be formed in one unit with a through-hole therein, and the threaded-portion 15a may be implemented by another separate part, such as a long bolt, to be fastened to a fixture through the through-hole.

The implant jig 20 according to the second embodiment, is similar to the implant jig according to the first embodiment described above, and includes a coupling portion that supports a bite material, a connecting portion that is coupled to an embedded fixture, and a body that is formed between the coupling portion and the connecting portion.

However, the implant jig 20 according to the second embodiment is different from the implant jig according to the first embodiment in that the coupling portion 22 and the body 23 are implemented in an outer body member 21 that is one unit and the connecting member 25 that is a separate part is inserted in the through-hole in the outer body member 21.

In the second embodiment, the though-hole formed in the outer body member 21 is composed of a small-diameter body portion 21a having a small diameter, a large-diameter body portion 21b formed at the coupling portion 22 and having a large diameter, and a tapered body portion 21c that is formed between the large-diameter body portion 21b and the small-diameter body portion 21a to gradually decrease in diameter. In this structure, the tapered body portion 21c does not necessarily gradually decrease in diameter and may be implemented in any shape as long as the outer body member 21 can be fixed by the connecting member 25.

Meanwhile, the connecting member 25 has a small-diameter connection portion 25a having a diameter corresponding to the small-diameter body portion 21a, a large-diameter connection portion 25b having a diameter corresponding to the large-diameter body portion 21b, a tapered connection portion 25c having a shape corresponding to the tapered body portion 21c, and a threaded-portion 25d having a thread to be fastened to a fixture embedded in the gums.

With the tapered connection portion 25c of the connecting member 25 in contact with the tapered body portion 21c of the outer body member 21, the outer body member 21 can be fixed on the fixture by fastening the threaded portion 25d of the connecting member 25 to the fixture.

In the second embodiment, similar to the first embodiment, a driver seat hole 27 is formed in the coupling portion 22 and a bored portion 27b is formed at the inlet of the driver seat hole 27.

FIGS. 7A-7C show examples of various shapes of implant jigs according to the second embodiment. As with the first embodiment, it is possible to manufacture and use various shapes of implant jigs, in accordance with the conditions of the patient's mouth or the types of fixtures.

Hereinafter, according to one embodiment, a process of taking a bite impression in the course of manufacturing an implant prosthesis is described with reference to FIGS. 8A-8G.

According to the illustrated embodiment, (a) a dental impression is taken, (b) which will be sent to a dental laboratory, (c) following the dental impression, an implant jig is fastened to a fixture embedded in the patient's gums, (d) a bite impression is taken by depositing a bite material, after which the patient holds the teeth tightly together as the material hardens, to form an impression of the relationship between the upper and lower teeth as they meet, (e) the bite impression is sent with the dental impression material to the dental laboratory, (f) models of the patient's teeth are made, and (g) the prosthesis is manufactured by using the dental impression and the bite impression. It is preferable to separate the implant jig from the fixture after taking the bite impression.

From the dental impression, the manufacturer can make a precise model of the patient's teeth and gums, including the space in which the prosthesis must be positioned. A hollow space can be provided in the general area of the gums around where the fixture is embedded. The manufacturer positions a duplicate implant jig in the space formed in the bite impression by the implant jig, and then positions the bite impression between the upper and lower sections of the model. This will result in the implant jig being supported by the bite impression in the same position the jig was in when the bite impression was taken, with the connection portion of the jig being supported in the hollow space provided. The hollow space is then filled in around the connection portion of the jig with modeling material, which is then cured. After curing, the implant jig is removed from the model, leaving behind a socket in the precise position of the fixture embedded in the patient's gums. The prosthesis can then be made to engage the embedded fixture and correctly fit in the patient's mouth, without the need for a return to the hospital for a bite impression after the implant abutment is installed.

The prosthesis manufactured in the dental laboratory is sent to the hospital, the patient comes to the hospital, and the prosthesis is attached to the fixture in the patient's mouth, thereby completing the implant operation.

As described above, according to an embodiment, since it is possible to take a bite right after taking the impression, it is possible to prepare all steps for manufacturing a prosthesis in one visit of the patient. Therefore, it is possible to reduce the time and cost for the operation, as compared with the related art in which a jig for supporting is separately manufactured in a dental laboratory and sent to a dental clinic and the patient has to come again to the clinic in order to take a bite impression.

As described above, it is possible to simultaneously take a dental impression and a bite impression in the process of manufacturing the prosthesis in the operation of an implant, by the implant jig of the present invention, such that it is possible to reduce the time and cost for manufacturing the prosthesis and take an accurate bite impression.

As described above, according to an embodiment, it is possible to provide an implant bite registration jig and a bite impression fabrication method using the jig, which make it possible to simultaneously take the dental impression and a bite impression in an implant operation, similar to a natural teeth operation. Therefore, it is possible to reduce the cost and time for manufacturing the prosthesis.

Although an implant bite registration jig and a bite impression fabrication method using the jig according to various embodiments have been described above with reference to the exemplary drawings, the present invention is not limited to the disclosed embodiments and the drawings, and may be changed and modified in various ways by those skilled in the art.

It will be apparent to those skilled in the art that various modifications and variations can be made to the embodiments in light of the above-detailed description without departing from the spirit or scope of the invention.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An implant bite registration jig for fastening to a fixture embedded in a patient's gums so as to take a bite impression, and for separating from the fixture after taking the bite impression, the implant bite registration jig comprising:
    a coupling portion that supports a bite material, the coupling portion including a cylindrical upper section having a constant diameter followed by an inclined lower section in which the diameter of the inclined lower section is gradually reduced with increasing distance from the upper section;
    a connecting portion configured to connect the implant jig with the fixture embedded in the patient's gums via a section of the connecting portion having threads and a cylindrical, non-threaded portion above the threads; and
    a body that is formed between the coupling portion and the connecting portion, the body including a cylindrical section having a body diameter that is smaller than the constant diameter of the upper section of the coupling portion and that smoothly transitions from the inclined lower section of the coupling portion,
    wherein the implant bite registration jig has a driver seat hole that is formed in a polygonal prism shape through a top of the coupling portion so as to receive a fastening tool for assembling or separating the implant jig with or from the fixture and to enable removal of the bite material after the bite impression is taken,
    wherein a bored portion having a diameter larger than a cross-section of the driver seat hole is formed at an inlet of the driver seat hole,
    wherein the bored portion is stepped,
    wherein the bite material can be received in a volume of the bored portion so that an amount of the bite material received in the driver seat hole is reduced in taking the bite impression, and
    wherein an inner surface of the driver seat hole and an inner surface of the bored portion are shaped to enable removal of the bite material.

2. The implant bite registration jig according to claim 1, wherein the top of the coupling portion is flat, and smooth without prominences and depressions.

3. The implant bite registration jig according to claim 1, wherein edges on outer sides of the coupling portion and the body are rounded.

4. The implant bite registration jig according to claim 1, wherein the driver seat hole is configured to receive a same fastening tool as is used for implant operation, and the driver seat hole is sized such that the fastening tool is friction-fitted.

5. A method, comprising:
    attaching the implant bite registration jig of claim 1 to a fixture that is embedded in a patient's gum;
    taking a bite impression in the patient's mouth, including an impression of a top portion of the registration jig to a sufficient depth to permit accurate repositioning of the registration jig in the resulting bite impression;
    taking a dental impression of the patient's teeth; and
    obtaining sufficient information from the dental impression and the bite impression to manufacture a dental implant properly formed to be mounted in an aperture of the fixture.

6. An implant bite registration jig for fastening to a fixture embedded in a patient's gums so as to take a bite impression, and for separating from the fixture after taking the bite impression, comprising:
    a body having first and second ends;
    a coupling portion at the first end of the body, having a shape configured to produce a clear reference mark in a bite impression material, to be separable, once the impression material is sufficiently cured, from a resulting bite impression without damaging the reference mark, and to be received by the reference mark so as to be securely held by the bite impression, the coupling portion including a cylindrical upper section having a constant diameter greater than a diameter of the body which is followed by an inclined lower section in which the diameter of the inclined lower section is gradually reduced with increasing distance from the upper section to smoothly transition into the first end of the body; and
    a connecting portion at the second end of the body, configured to engage an aperture in an implant fixture via a section of the connecting portion having threads and a cylindrical, non-threaded portion above the threads,
    wherein the implant bite registration jig has a driver seat hole that is formed in a polygonal prism shape through a top of the coupling portion so as to receive a fastening tool for assembling or separating the implant jig with or from the fixture and to enable removal of the bite material after the bite impression is taken,
    wherein a bored portion having a diameter larger than a cross-section of the driver seat hole is formed at an inlet of the driver seat hole,
    wherein the bored portion is stepped,
    wherein the bite material can be received in a volume of the bored portion so that an amount of the bite material received in the driver seat hole is reduced in taking the bite impression, and
    wherein an inner surface of the driver seat hole and an inner surface of the bored portion are shaped to enable removal of the bite material.

* * * * *